United States Patent [19]

McNally

[11] 4,045,177

[45] Aug. 30, 1977

[54] APPARATUS FOR DETECTING COMBUSTIBLE GASES

[75] Inventor: Frank X. McNally, Venetia, Pa.

[73] Assignee: CSE Corporation, Monroeville, Pa.

[21] Appl. No.: 714,602

[22] Filed: Aug. 16, 1976

[51] Int. Cl.² .......................................... G01N 27/16
[52] U.S. Cl. .................................... 23/254 E; 338/34
[58] Field of Search ............ 23/254 E, 255 E, 232 E; 73/27 R; 338/34; 340/237 R

[56] References Cited

U.S. PATENT DOCUMENTS

| 3,092,799 | 6/1963 | Baker | 338/34 |
| 3,117,843 | 1/1964 | Baker | 23/254 E |
| 3,200,011 | 8/1965 | Baker | 23/254 E X |
| 3,564,474 | 2/1971 | Firth et al. | 23/254 E X |

Primary Examiner—Joseph Scovronek

[57] ABSTRACT

This is an improvement in apparatus for detecting combustible gases, such as methane, that embodies a Wheatstone bridge circuit including a refractory-coated reference element constituting one leg of the bridge and a refractory-coated detector element having thereon a catalyst for promoting oxidation of the combustible gas to be detected constituting a second leg of the bridge. Upon oxidation of combustible gas at the detector element the temperature and resistance thereof increases relative to the reference element to unbalance the bridge, thereby producing an electrical signal proportional to the amount of combustible gas being oxidized. This invention improves the stability, linearity, and stabilization time of the bridge signal by constructing the reference element so that at zero percent combustible gas or during oxidation of the combustible gas at the detector element the radiant energy of both the detector and reference element are substantially equal.

6 Claims, 1 Drawing Figure

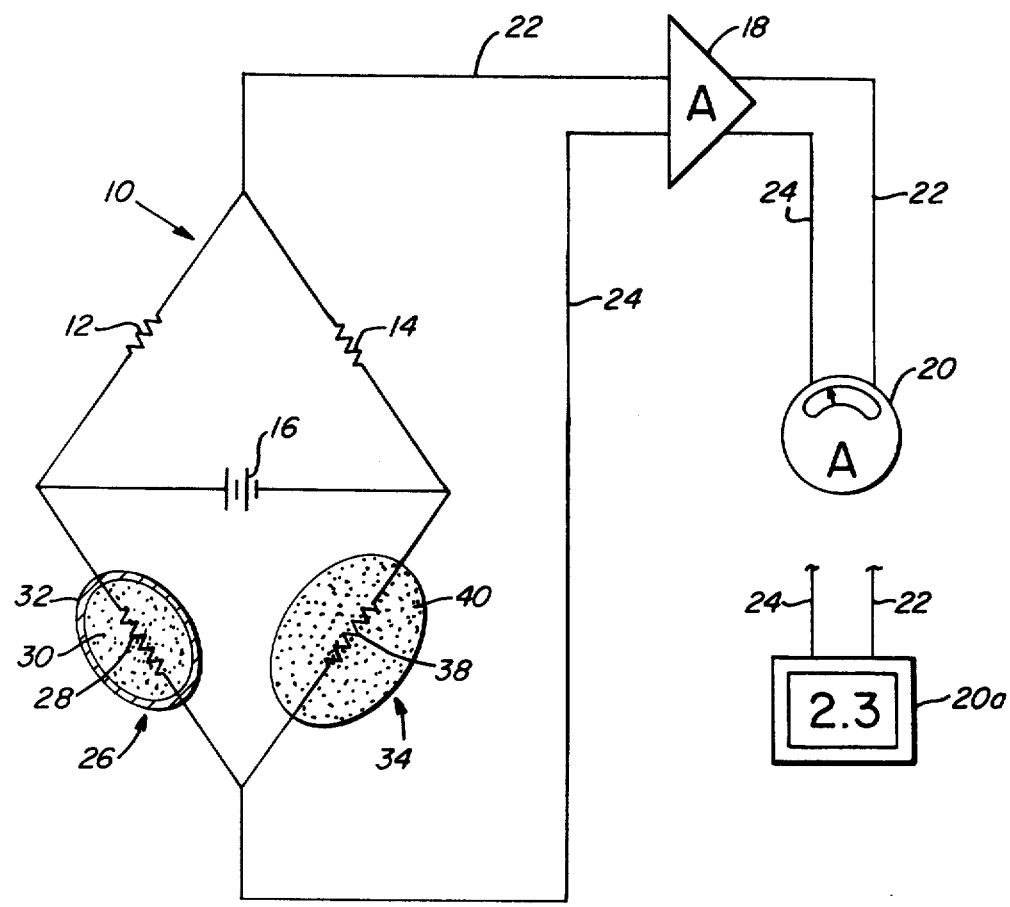

APPARATUS FOR DETECTING COMBUSTIBLE GASES

In various industrial applications it is necessary to have apparatus for detecting the presence of combustible gases. Specifically, in coal mines it is required that workers have means to indicate the presence of methane in the mine atmosphere. It is necessary that the detecting means provide an accurate indication of the level of any methane present so that minimg personnel may evacuate any area at which th methane content in the atmosphere reaches a level prescribed as unacceptable for safe working. For this application it is common to use a methane detector embodying a Wheatstone bridge circuit having fixed resistances together with two electrically conducting members having finite temperature coefficients. These electrically conducting members are coated with a refractory material, such as alumina. One of the electrically conducting members constituting one leg of the bridge is constructed of a platinum coil as the conductive element which is then covered with the refractory. This element constitutes the reference element of the detector. The other leg of the bridge is similarly constructed except that a catalyst for promoting the oxidation of methane, which may be platinum or palladium black or combinations thereof, is applied over the refractory material. This element is the detector element. In operation, upon exposure of the detector element to methane, catalytic oxidation of the methane occurs. If, in the absence of methane at the detector element, there is a constant bridge voltage with the bridge being balanced; upon encountering methane with subsequent catalytic oxidation of methane, the temperature at the detector element will rise. This, in turn, causes a rise in the resistance of the platinum coil of the detector element relative to the resistance of the other leg of the bridge constituting the reference element. Consequently, as is well known, the current through the detector element decreases and an increase in voltage across the detector element occurs relative to the reference element and the output signal of the bridge, which is now unbalanced, increases proportional to the change in resistance at the detector element. The change in resistance at the detector element is approximately proportional to the level of oxidation of methane at the detector and thus approximately proportional to the level of methane in the ambient atmosphere at the detector element. This bridge signal is consequently approximately proportional to the methane level in the atmosphere at the detector element and accordingly increases as the methane level, and thus oxidation at the detector element, increases. The electrical signal from the bridge is customarily amplified and used to provide either an analogue or digital readout of the degree of methane present in the atmosphere.

In methane detecting apparatus of this type it has been found that the output signal of the bridge indicating the level of methane in the atmosphere is characterized by instability and poor linearity. Broadly, this is caused by the difference in resistance across the detector element and reference element being affected by changes other than those caused by the catalytic oxidation of methane. Specifically, these resistance changes can be caused by changes in ambient temperature, and changes in the bridge voltage. In the present of a bridge voltage change or as a result of ambient temperature change the temperatures of the detector and reference elements do not remain uniform and a zero drift can result at zero percent methane. The emissivity of the detector coil is greater than the emissivity of the reference coil. Hence, the detector coil radiates energy at a rate greater than the reference coil. The high emissivity of the detector coil results from the catalyst, which is customarily platinum or palladium black, and is characterized by a significantly higher emissivity than the refractory coating of the reference element, which is typically alumina. Typically, the emissivity of the detector element having platinum or palladium black would be 0.9; whereas, the emissivity of the reference element being pure alumina would be 0.1 to 0.2. Because of this nonuniform change in the temperatures of the detector and reference element a relatively long time is required for stabilization at zero percent methane. In the presence of methane, the relative resistances thereof during catalytic oxidation of methane will change other than as a result of said oxidation. This relative change or relative difference in resistance not resulting from catalytic oxidation of methane and thus nonlineraly proportional to the level of methane in the atmosphere at the detector coil will accordingly result in a bridge output signal and a corresponding methane readout not linearly proportional to said methane level. As above mentioned, this will result during changes in ambient temperature or bridge voltage thus rendering the output of the bridge unstable and inaccurate, and can cause a zero drift wherein the instrument may indicate a finite value of percent methane in the absence of methane. Likewise, in the presence of increased methane levels and increased oxidation at the detector coil, the resistance and thus temperature of the coil will increase but because of the difference in emissivity between the detector and reference coil the increased energy radiation from the detector coil will result in a temperature and resistance differential which is not linearly proportional to increased methane level in the atmosphere.

It is accordingly the primary object of the present invention to improve the linearity of response of methane detectors and minimize the instability thereof by controlling the emissivity and thus energy radiation from both the detector and reference elements during any changes in ambient temperature and/or bridge voltage.

It is also an object of the invention to minimize the zero drift or change in zero indication in the absence of methane during any changes in ambient temperature and/or bridge voltage.

These and other objects of the invention, as well as a more complete understanding thereof, may be obtained from the following description, specific examples and drawing, in which the single FIGURE thereof is a schematic showing of a Wheatstone bridge and associated electrical circuit embodying one example of the present invention and adapted for use in a methane detector functioning by the catalytic oxidation of methane.

Broadly in accordance with the present invention a conventional apparatus for detecting combustible gases, such as methane, includes a Wheatstone bridge circuit having a reference element comprising an electrically conducting member coated with a refractory with said reference element constituting one leg of the bridge. A detector element having an electrically conducting member with the conductive element coated with a like refractory and on the surface thereof a catalyst for the oxidation of the combustible gas, such as methane, constitutes the other leg of the bridge. Upon the catalytic oxidation of the gas an electrical signal approximately proportional to the amount of said gas present at the detector element is produced across the bridge. This signal is approximately proportional to the methane level in the atmosphere and is used to provide a readout. In accordance with the present invention specifically, this otherwise conventional apparatus is modified by adjusting the emissivity and thus the energy radiation of the reference element so that it is substantially linearly proportional to the relative increase in the energy radiation of the detector element resulting from the increased emissivity produced by and characteristic of the catalyst thereon. More specifically, in accordance with the present invention this can be achieved by increasing the thickness (i.e., the diameter) of the refractory coating on the reference element relative to the thickness of the coating on the detector element with said increased thickness (i.e., diameter) being that required to compensate for the relative increase in radiant energy imparted to the detector element by the higher emissivity of the catalyst thereon. In this manner, the radiant energy of the reference element and the detector element are made substantially equal at zero percent methane. Consequently, in the presence of changes affecting these elements, which may be either changes in ambient temperature or bridge voltage, the energy radiation from each will be substantially the same at zero percent methane and also, in the presence of methane, relative differences in temperature and resistance will be related to and proportional to only the oxidation of methane and thus the level of methane in the atmosphere at the detector element. This then reduces the instability of the signal from the Wheatstone bridge and makes it linearly proportional to any increase in methane level at the detector element. Hence, as the level of methane in the atmosphere at the detector element increases to increase the oxidation rate at the detector element the signal from the bridge will increase linearly with said increased methane level.

Alternately, the radiant energy of the reference element may be adjusted by applying an emissivity-promoting composition onto the refractory coating thereof. This likewise increases the emissivity of the reference element to a level substantially equal to the emissivity level of the detector element, and consequently, the radiant energy from each element will be substantially equal at zero percent methane. Specifically, the emissivity-promoting composition may be an oxide selected from the group consisting of vanadium, columbium, tantalum, chromium, molybdenum, tungsten or uranium.

Typically, the conductive material used as the electrically conducting member in both the reference element and detector element may be platinum. The catalyst applied over the refractory of the detector element may be platinum or palladium black, both of which promote the oxidation of methane. It is possible that combinations of these might also be used.

Referring to the drawing there is shown in the single FIGURE thereof schematically a methane detector suitable for the practice of the invention and showing one typical embodiment of the invention. The methane detector has a Wheatstone bridge circuit generally designated as 10. The bridge 10 has two fixed resistors 12 and 14, and a source of potential 16. The output from the bridge is connected through amplifier 18 to an analogue meter 20 or a digital display 20a via conductors 22 and 24. The bridge 10 also embodies a methane-detector element designated generally as 26, and having platinum resistor coil 28 coated with alumina refractory 30 over which is coated a catalyst for methane oxidation designated as 32; this catalyst may be platinum or palladium black. Likewise, the bridge 10 has a reference element, designated generally as 34. The reference element has a platinum resistor coil 28 coated with alumina refractory 40.

By the proper selection of resistors there is a zero output from the bridge circuit in the absence of methane at detector element 26. However, in the presence of methane, the methane is oxidized at the detector element 26, which oxidation is promoted by the catalyst 32, and the temperature of the platinum coil 28 as a result of the methane oxidation is increased. The temperature of the platinum coil 38 of reference element 34, however, remains unaffected as there is no oxidation of methane at this element. As the temperature of detector element 26 increases, relative to reference element 34 the resistance through coil 28 thereof correspondingly increases relative to the resistance of the coil 38 of reference element 34. Consequently, the bridge becomes unbalanced and a signal is produced via conductors 22 and 24 to amplifier 18. This signal is approximately proportional to the increase in resistance of the detector element 26 and accordingly the oxidation of methane at this detector, which in turn is approximately proportional to the amount or level of methane in the atmosphere at the detector element. The signal is amplified at amplifier 18 and introduced to an analogue ammeter 20 which may be calibrated to provide a readout proportional to methane in the atmosphere. However, in the case of a digital display, wherein digital circuitry is used, a highly linear signal is required.

In accordance with the invention the refractory coating 40 of reference element 34 surrounding platinum coil 38 is increased in thickness (i.e., diameter) relative to the refractory coating 30 surrounding the platinum coil 28 of detector element 26. The increased thickness (i.e., diameter) is that required to make the radiant energy proportional to the relative increased radiant energy imparted to the detector element by the increased emissivity of the catalyst 32 which is coated over the refractory 30. In this manner, as above described, any changes in the ambient temperature of changes in temperature of the elements caused by changes in bridge voltage, other than an increase in the temperature of element 28 of the detector element 26 resulting from oxidation of methane, will not result in a change of the relative resistance and thus result in an unstable and nonlinear output signal from the bridge to the meter or digital display. Alternately, as above described the thicknesses of the refractory coatings over the platinum resistance coils 28 and 38 may be maintained constant and the radiant energy may be controlled by applying over the refractory 40 an emissivity promoting composition, said composition being an oxide selected from the group of vanadium, columbium, tantalum, chromium, molybdenum, tungsten and uranium.

The following constitute specific examples of the practice of the invention.

EXAMPLE 1

A solution was prepared using vanadium pentoxide in an amount of 0.08 grams, distilled water in an amount of 2.5 ml, hydrochloric acid of a 30% concentration in an amount of 0.5 ml. This solution was applied in one microliter drops to the alumina coating on a reference element of the character earlier described. The solution was dried and thermally decomposed by passing a current varying from 20 milliamps to 50 milliamps through the reference element for a period of approximately two minutes. The reference element was in the form of a platinum resistance coil coated with alumina. The chemical reactions were as follows:

$$V_2O_5 + 2 HCl \rightarrow 2 VCl_2 + H_2O + 2O_2$$

$$VCl_2 + O_2 \rightarrow VO_2 + Cl_2$$

$$4VO_2 \rightarrow V_2O_3$$

This reference element was then placed in a Wheatstone bridge of the type shown in the FIGURE and described above and during testing to determine the zero drift of the bridge signal in the absence of methane, the following results as reported in TABLE I were obtained:

TABLE I

| Bridge Supply Voltage V | Bridge Signal Zero Percent Methane Zero Drift mV | |
|---|---|---|
| | Without Treatment | With Treatment |
| 2.6 | − 7.0 | − 2 |
| Normal 2.4 | 0 | 0 |
| 2.2 | + 7.0 | + 3 |

Table I indicates that the zero drift at zero percent methane has been reduced from ± 7 mV to approximately ± 3 mV with a bridge power supply excursion of ± 0.2 volts. This corresponds to a zero shift of an unsatisfactory ± 0.3% being reduced to a satisfactory ± 0.1%, when the error is expressed as percent methane on the display. Since the bridge power supply excursion of ± 0.2 volts heats or cools both detectors, this is similar to the effect that a change in ambient temperature produces.

EXAMPLE 2

A further test was conducted using a solution of uranyl nitrate in an amount of 0.5 grams, distilled water in an amount of 20 ml. This solution was applied to the reference element and treated in the same manner as described in Example 2. The chemical reactions were as follows:

$$UO_2(NO_3) \cdot 6H_2O \rightarrow UO_2(NO_3)_2 + 6H_2O$$

During testing of the reference element in the Wheatstone bridge circuit as earlier described the following results as reported in Table II were obtained:

TABLE II

| Bridge Supply Voltage V | Bridge Signal Zero Percent Methane Zero Drift mV | |
|---|---|---|
| | Without Treatment | With Treatment |
| 2.6 | − 4.4 | + 2.0 |
| Normal 2.4 | 0.0 | 0.0 |
| 2.2 | 4.5 | − 2.0 |

It may be noted that when the bridge voltage went to 2.6, the "without treatment" zero drift was minus 4.4 mV. However, "with treatment" as the bridge voltage went to 2.6 the zero shift was plus 2.0 mV. This indicates that too much correction was made in the emissivity of the reference element. Nevertheless, the zero drift error was reduced from an unsatisfactory 0.2% to a satisfactory 0.1% expressed as methane concentration error in the atmosphere at the display.

EXAMPLE 3

The same solution was used as in example 2 but less was applied to the reference element than in Example 2. The results are as follows and reported in Table III:

TABLE III

| Bridge Supply Voltage V | Bridge Signal Zero Percent Methane Zero Drift mV | |
|---|---|---|
| | Without Treatment | With Treatment |
| 2.6 | − 5.8 | − 1.5 |
| Normal 2.4 | 0 | 0 |
| 2.2 | + 4.0 | + 1.9 |

In this example, the zero shift due to bridge supply voltage change was reduced from approximately ± 4.9 mV to ± 1.7 mV which corresponds to reduction in the zero drift error of an unsatisfactory 0.2% to a highly satisfactory 0.0% expressed as methane concentration error on the display.

EXAMPLE 4 after treatment of a reference element as described in Example 2 (application of emissivity controlling uranium compounds) the results were as follows when the sensor was tested in a Wheatstone bridge.

TABLE IV

| Bridge Supply Voltage V | Bridge Signal Zero Percent Methane Zero Drift mV | |
|---|---|---|
| | Without Treatment | With Treatment |
| 2.6 | − 8.8 | − 1.4 |
| Normal 2.4 | 0 | 0 |
| 2.2 | + 5.7 | + 1.1 |

These results are similar to previous results. This detector was also mounted with and without treatment in a portable methane detector, and performance tested with the results as indicated in Table V.

TABLE V

| | Actual Percent Methane | Instrument Display Percent Methane | |
|---|---|---|---|
| | | Without Treatment | With Treatment |
| Room Temperature | 0 | 0.0 | 0.0 |
| 72% | 1.8 | 1.8 | 1.8 |
| After Cooling to | 0 | 0.3 (error) | 0.0 (no error) |
| 50° F | 1.8 | 1.5 (error) | 1.8 (no error) |

From this Table, it can be seen that the instrument exhibited essentially a zero temperature coefficient and no error over the temperature range tested, resulting from use of the new and improved gas sensor.

A further benefit of the application of the emissivity controlling compound, as described hereinabove is that the radiant energy from each element is equalized and the effect is that the overall stabilization time is considerably reduced at zero percent methane and also reduced to a lesser extent in the presence of methane. The following Table VI adds additional data to Example 4.

TABLE VI

| Actual Percent Methane | Instrument Display Percent Methane | |
|---|---|---|
| | Without Treatment Stabilization Time | With Treatment Stabilization Time |
| 0.0 | 12 seconds | 4 seconds |
| 1.8 | 15 seconds | 8 seconds |
| 3.4 | 15 seconds | 10 seconds |

The following constitutes a specific example of the invention wherein the radiation from the reference element was regulated by increasing the thickness (i.e., diameter) of the refractory coating over the platinum coil to effect a substantial improvement in linearity.

EXAMPLE 5

TABLE VII

| Actual Percent Methane | Percent Methane Displayed by Instrument | | | |
|---|---|---|---|---|
| | Refractory Diameter of Elements | | Refractory Diameter of Elements | |
| | Detector 0.53" | Reference .055" | Catalyst .053" | Reference .065" |
| 0 | 0.0% | | 0.0% | |
| 1.0 | 0.8% | (error) | 1.0% | (no error) |
| 2.0 | 2.0% | (no error)* | 2.0% | (no error) |
| 3.0 | 3.9% | (error) | 3.1% | (no error) |

*Instrument is calibrated at 2% methane and thus there is "no error"; errors appear at other methane concentrations due to nonlinearity.

The control and adjustment of the reference refractory diameter, relative to the catalyst, provides an improvement in the linearity of the instrument.

I claim:

1. In an apparatus for detecting a combustible gas, such as methane, by a combination including a Wheatstone bridge circuit having a reference element comprising an electrically conducting member coated with a refractory, said reference element constituting one leg of said bridge, a detector element comprising an electrically conducting member coated with a refractory and having on the surface of said refractory a catalyst for the oxidation of said gas, said detector element constituting a second leg of said bridge, whereby upon catalytic oxidation of said gas an electrical signal approximately proportional to the amount of said gas present at the detector element is produced, the improvement comprising means at said reference element which increases its emissivity to the same emissivity as that of said detector element, whereby the energy radiation of the reference element is substantially linearly proportional to the energy radiation of the detector element during oxidation of said combustible gas at said detector element.

2. In an apparatus for detecting a combustible gas, such as methane, by a combination including a Wheatstone bridge circuit having a reference element comprising an electrically conducting member coated with a refractory, said reference element constituting one leg of said bridge, a detector element comprising an electrically conducting member coated with a refractory and having on the surface of said refractory a catalyst for the oxidation of said gas, said detector element constituting a second leg of said bridge, whereby upon catalytic oxidation of said gas an electrical signal approximately proportional to the amount of said gas present at the detector element is produced, the improvement comprising the refractory coating on said reference element being thicker than the refractory coating on said detector element, said increased thickness being proportional to the relatively increased energy radiation imparted to said detector element by said catalyst, whereby the energy radiation of the reference element is substantially linearly proportional to the energy radiation of the detector element during oxidation of said combustible gas at said detector element.

3. In an apparatus for detecting a combustible gas, such as methane, by a combination including a Wheatstone bridge circuit having a reference element comprising an electrically conducting member coated with an alumina refractory, said reference element constituting one leg of said bridge, a detector element constituting a second leg of said bridge and comprising an electrically conducting member coated with an alumina refractory and having on the surface of said alumina refractory a catalyst for the oxidation of said gas, said catalyst being selected from the group consisting of platinum, palladium black and combinations thereof, whereby upon catalytic oxidation of said gas an electrical signal approximately proportional to the amount of said gas present at the detector element is produced, the improvement comprising means at said reference element which increases its emissivity to the same emissivity as that of said detector element, whereby the energy radiation of the reference element is substantially linearly proportional to the energy radiation of the detector element during oxidation of said combustible gas at said detector element.

4. In an apparatus for detecting a combustible gas, such as methane, by a combination including a Wheatstone bridge circuit having a reference element comprising an electrically conducting member coated with a refractory, said reference element constituting one leg of said bridge, a detector element comprising an electrically conducting member coated with a refractory and having on the surface of said refractory a catalyst for the oxidation of said gas, said detector element constituting a second leg of said bridge, whereby upon catalytic oxidation of said gas an electrical signal approximately proportional to the amount of siad gas present at the detector element is produced, the improvement comprising said reference element having a coating of an emissivity-promoting composition on the refractory thereof, whereby the energy radiation of the reference element is substantially linearly proportional to the energy radiation of the detector element during oxidation of said combustible gas at said detector element.

5. The apparatus of claim 4 wherein said emissivity-promoting composition is an oxide selected from the group of oxides of vanadium, columbium, tantalum, chromium, molybdenum, tungsten and uranium.

6. In an apparatus for detecting a combustible gas, such as methane, by a combination including a Wheatstone bridge circuit having a reference element comprising an electrically conducting member coated with an alumina refractory, said reference element constituting one leg of said bridge, a detector element constituting a second leg of said bridge and comprising an electrically conducting member coated with an alumina refractory and having on the surface of said alumina refractory a catalyst for the oxidation of said gas, said catalyst being selected from the group consisting of platinum, palladium black and combinations thereof, whereby upon catalytic oxidation of said gas an electrical signal approximately proportional to the amount of said gas present at the detector element is produced, the improvement comprising the alumina refractory coating on said reference element being thicker than the alumina refractory coating on said detector element, said increased thickness being proportional to the relative increased energy radiation imparted to said detector element by said catalyst, whereby the energy radiation of the reference element is substantially linearly proportional to the energy radiation of the detector element during oxidation of said combustible gas at said detector element.

* * * * *